United States Patent [19]

Storz

[11] 4,449,532

[45] May 22, 1984

[54] DILATOR TO FACILITATE ENDOSCOPE INSERTION INTO THE BODY

[76] Inventor: Karl Storz, Auf dem Schildrain 39, 7200 Tuttlingen, Fed. Rep. of Germany

[21] Appl. No.: 280,057

[22] Filed: Jun. 30, 1981

[30] Foreign Application Priority Data

Jul. 8, 1980 [DE] Fed. Rep. of Germany ....... 3025785

[51] Int. Cl.³ ............................................ A61M 29/00
[52] U.S. Cl. ...................................... 128/341; 128/20; 128/4
[58] Field of Search ................. 128/20, 341, 342, 343, 128/4, 6

[56] References Cited

U.S. PATENT DOCUMENTS

| | | | |
|---|---|---|---|
| 2,707,956 | 5/1955 | Koff | 128/341 |
| 3,196,876 | 7/1965 | Miller | 128/343 |
| 3,344,791 | 10/1967 | Foderick | 128/343 |
| 3,630,190 | 12/1971 | Baker | 128/341 |
| 3,789,852 | 2/1974 | Kim et al. | 128/343 |

FOREIGN PATENT DOCUMENTS 258116 4/1912 Fed. Rep. of Germany ...... 128/343

*Primary Examiner*—Kyle L. Howell
*Assistant Examiner*—Max F. Hindenburg

[57] ABSTRACT

A dilator for surgical use having a ball on the end of a thin stiff stem. A plurality of telescoping tubes are adapted to be slid along the stem and atop one another so as successively to enlarge the path opened by the dilator. An endoscope shaft can be slid over the set of tubes so as to occupy the region they have enlarged, and to permit them and the probe to be withdrawn so an endoscopic procedure can be performed.

8 Claims, 7 Drawing Figures

U.S. Patent  May 22, 1984  4,449,532
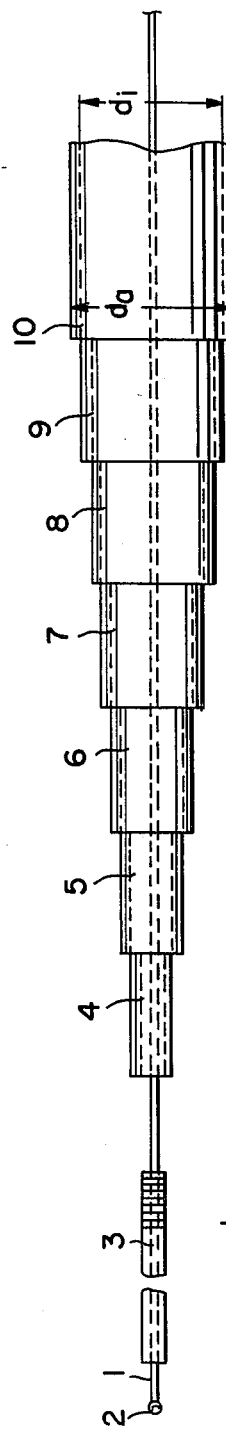
FIG.1
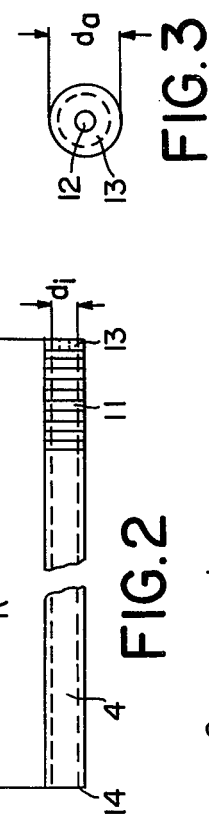
FIG.2
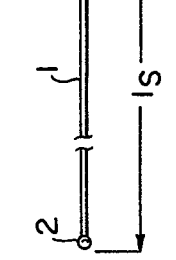
FIG.3
FIG.4
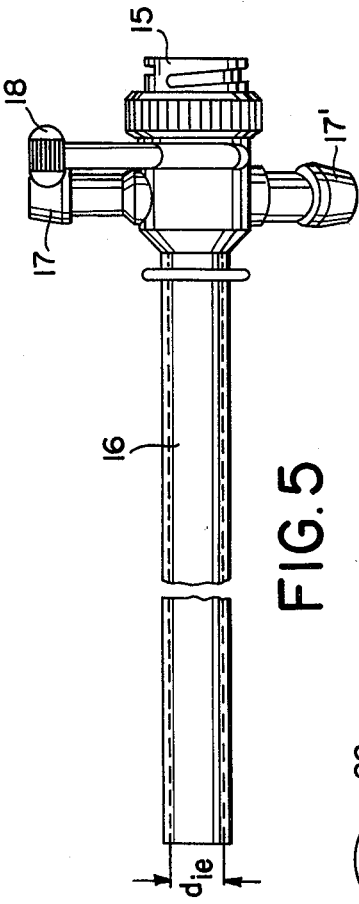
FIG.5
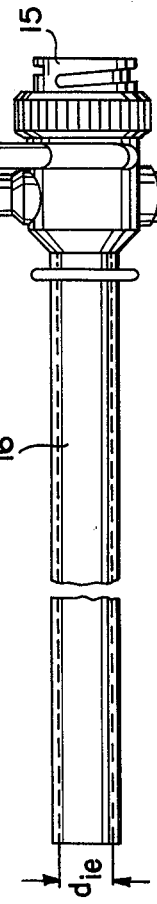
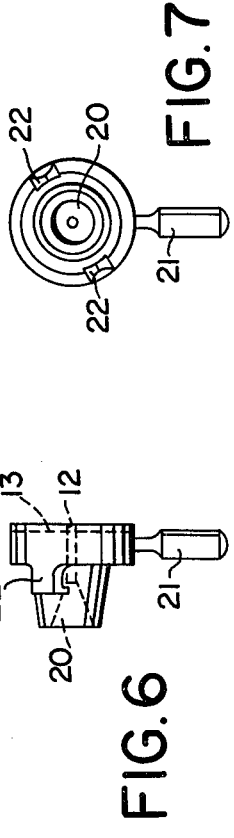
FIG.6
FIG.7

DILATOR TO FACILITATE ENDOSCOPE INSERTION INTO THE BODY

BACKGROUND OF THE INVENTION

The invention relates to a dilator for the insertion of medical endoscopes for performing operations or examinations with a supporting probe on whose end is arranged a ball onto which can be shoved a plurality of dilation tubes having successively larger diameters.

Endoscopes are inserted into body cavities by means of sharp trocars with a trocar cannula, the trocar being removed after the sharp insertion for the purpose of introducing the endoscope through the trocar cannula. The said cannula can have a device for increasing the friction resistance against axial displacement such as a strip-like material of limited wall thickness applied spirally to the trocar cannula and also fixed to it. This significantly reduces frictional resistance on inserting and removing the trocar cannula without the diameter of the latter having to be very large, such a construction is shown in German Patent No. 2,218,901.

However, an operation by means of a trocar obviously represents a considerable risk and produces a large residual scar, because from the outset the sharp trocar tip produces a correspondingly large wound.

It has therefore long been standard practice to carry out dilation by means of a dilator of the aforementioned type, and it is then usual under X-ray examination to insert the probe with a ball on its tip into the kidney region, as an example. The probe can be very thin and can therefore be much moe easily introduced than the trocar tip. When the probe has reached the desired point in the human body, then according to the prior art successively a plurality of dilation tubes with an increasing diameter are advanced on the probe up to the ball. However, the procedure has always hitherto been such that before inserting a next tube with somewhat larger diameter, the preceding tube is completely removed from the cavity and from the probe. However, this leads to the opening becoming constricted somewhat again, so that the desired expansion action is partly cancelled out. This is among other things due to the fact that after removing a certain size tube, for example when operating on the esophagus, the latter shrinks again in the vicinity of a stenosis, which must be additionally expanded with the next dilation tube size.

BRIEF SUMMARY OF THE INVENTION

The problem of the invention is to obviate this serious disadvantage and to so improve the dilator of the aforementioned type that there is no shrinkage of the dilated tissue before the next tube is inserted.

This problem is solved by this invention. It provides the possibility of inserting the following dilation tube without removing the preceding tube to form a path into the human body. Thus, the invention reliably ensures that there is no shrinkage of the dilated tissue. This not only greatly facilitates the operation, but also significantly protects the patient's tissue and the incremental increases can be a little larger than in the prior art. During the operation the relative movement between the dilator and the patient's tissue is significantly reduced.

The invention is mainly directed at the treatment of the kidneys, so that after dilation a lithotriptoscope can be inserted and the kidney stones removed. Another possibility is to insert an ultrasonic probe for destroying the kidney stones.

An optional feature of this invention makes it possible to remove, in addition to the first tube which is moved by the ball on the probe, all the other shoved-on tubes, together with the first tube and the probe. It would otherwise be necessary to greatly increase the size of the ball, which would naturally be highly disadvantageous.

Yet another optional feature of the invention greatly facilitates the manipulations compared with the prior art. The possibility exists of introducing the dilation tubes in rapid succession, which saves a great deal of operating time.

BRIEF DESCRIPTION OF THE DRAWINGS

The invention is described in greater detail hereinafter relative to non-limitative embodiments and the attached drawings, in which:

FIG. 1 is a diagrammatic side view of the overall arrangement.

FIG. 2 is a side view of a dilation tube alone.

FIG. 3 is a plan view of the distal end of one of the tubes 4 to 10.

FIG. 4 is a side view of the probe alone.

FIG. 5 is a side view of an endoscope shaft alone.

FIG. 6 is a side view of the closing cap for the endoscope shaft.

FIG. 7 is a front view of the cap of FIG. 6.

DETAILED DESCRIPTION OF THE PREFERRED EMBODIMENTS

In FIG. 1 the relative sizes are not correctly reproduced and for illustrative purposes the dimensions are partly shown much larger and partly much smaller, which enables the complete installation to be shown.

To the left it is possible to see probe 1 with ball 2 at the distal end. The probe is formed e.g. by a steel wire with the diameter of only 1 mm. Onto the probe is firstly placed the first dilation tube 3 in its internal diameter $d_i$ is only large enough to ensure that the wire 1 fits in it with a clearance. Tube 3 is much longer than shown, it being shortened in the drawings solely to make it possible to show all the other tubes 4 to 10 which other tubes have sequentially increasing diameters. According to the invention the internal diameter $d_i$ and external diameter $d_a$ are so matched to one another that the connecting tubes to the right, i.e. 4 to 6 are telescopable. This means that the particular external diameter $d_a$ can be fitted with a clearance into the opening of the following tube with the diameter $d_i$ with a slight clearance fit. Naturally tube 3 fits into tube 4 in the same way, although this is not shown.

At the right end of the arrangement of FIG. 1 it is again possible to see probe 1 projecting beyond the final tube 10. FIG. 2 shows tube 4 only, whose length $l_r$ is shown much reduced in the drawings. The internal diameter $d_i$ is such that tube 3 with its external diameter $d_a$ is inserted with a slight clearance fit. The distal end 14 of tube 4 is completely open, whilst the proximal end is closed by plate 13, having a central bore solely for the passage of the probe 1. In addition, at the proximal end of tube 4 there are grooves 11 at right angles to its longitudinal direction.

All the other tubes 5 to 10 are constructed in the same way as tube 4. Only in the case of tube 3 is the closure plate 13 not provided, this being impossible with the indicated dimensions.

FIG. 3 is a front view of the closure plate 13 with central bore 12 for the passage of probe 1.

FIG. 4 shows this probe 1 alone. It is formed by a rigid wire, on whose left-hand end is provided ball 2, which stops the forward movement of the first tube 3. The length of the tubes. Length $l_s$ of probe 1 is preferably double the length l of all tubes 3 to 10 are preferably equal to one another.

Finally FIG. 5 shows the endoscope shaft 16 with its internal diameter $d_{ie}$ in which there is introduced with a clearance fit the dilation tube 10 with its external diameter $d_a$. At the right-hand proximal end is provided the conventional bayonet catch 15, known supply lines 17' and 17 and a change lever 18. Endoscope shafts of this type are known per se and need not therefore be described in detail. According to the invention it is only important for the said external diameter $d_a$ of the last tube 10 to be adapted in the indicated manner to the free opening of the endoscope shaft.

The diameter steps can be such that the external diameter of endoscope shaft 16 is only 8 mm, so that the difference $d_a - d_i$ of each tube is less than 1 mm if the probe is 1 mm thick. However, it is not difficult to make such small wall thicknesses for the steel tubes 3 to 10.

When using the device, initially only probe 1 is inserted in the patient's body in the known manner. However, this is followed not by the first expansion tube 3 alone, but preferably by simulaneously placing all the tubes 3 to 10 on probe 1, as shown in FIG. 3. The first tube 3 can then be inserted alone. The remaining tubes 4 to 10 can follow in rapid succession without leaving the telescopic arrangement. The endoscope shaft 16 can be placed over the final tube 10. Probe 1 is long enough to initially separate the furthest forward dilation tube completely from the others to enable grasping of grooves 11. Prior to fitting the endoscope shaft or subsequently the endoscope can be fitted with the closing cap 19 which can be screwed onto the bayonet catch 15. Inlet cone 20 permits the easy insertion of probe 1 into the closure plate 13 on the inlet cone. Although it is possible to work without cap 19 it leads to the danger of endoscope shaft 16 being shoved too far onto tube 10. Cap 19 in fact forms a stop member with respect to the final tube 10. When the endoscope shaft is moved so far along the tubes that tube 10 strikes cap 19, the distal end of the endoscope shaft will be about even with the distal ends of tubes 4–10. Then the bayonet catch can be released, and the distal end of the probe (which projects proximally beyond it) can be pulled so as to draw the tubes out of the endoscope shaft, leaving the endoscope shaft in place of the tube, and with the endoscope shaft open to receive endocopic instruments. Cap 19 comes away with the tubes. This involves no effort and in no way stresses the patients' tissue. By means of ball 2 the innermost tube 3 and through the latter in the contact sequence of closure plates 13 of the remaining tubes 4 to 10, all the tubes can be safely and reliably removed. In per se known manner an endoscope can now be introduced into endoscope shaft 16.

In the case of kidney treatment it can preferably be kidney stone forceps or a lithotriptoscope. However, it is also possible to insert an ultrasonic probe for destroying the kidney stones. This makes it possible to avoid a major kidney operation.

The invention is not limited to the embodiment shown. In particular the reciprocal stopping of tubes 4 to 10 for removal purposes can be effected in some way other than by closure plates 13. For example any stop member between each pair of tubes would be sufficient to enable the removal from endoscope shaft 16 of all the tubes to the right in FIG. 1, together with the innermost tube 3. It would also be possible to provide a similar stop member at least temporarily at the distal end of endoscope shaft 16 in place of closure cap 19 to limit the introduction of the shaft on the final tube 10. In this case the projections 22 of cap 19 would merely be adapted to the bayonet catch 15 because the latter are generally provided on endoscope shafts 16 for stopping the endoscopes. Thus, there is no need to modify endoscope shaft 16 for the purpose of performing the invention.

What is claimed is:

1. A dilator for opening a path in the human body for the subsequent introduction of an endoscope shaft, said dilator having a distal end to enter the body, and a proximal end, comprising: a probe comprising a stiff rod and a ball on the end of said rod; and a plurality of expansion tubes adapted sequentially to enlarge a path formed by the introduction of the probe, ball first, into the body, each said tube having an inside and an outside diameter, the outside diameter of one tube being substantially equal to the inside diameter of the next larger tube, whereby to permit a close sliding axial telescopic fit, said rod being within and extending beyond said expansion tubes whereby the path opened by the ball can be incrementally opened by pressing next sequential tubes toward said ball.

2. A dilator according to claim 1 wherein each of said tubes, except for the smallest diameter tube, is provided at its proximal end with a closure plate having a bore for the passage of the probe therethrough, and for abutment by the closure plate of the next large tube.

3. A dilator according to claim 1, wherein in the vicinity of their proximal end, the tubes have grooves for grasping.

4. A dilator according to claim 1 wherein said probe is at last twice as long as any said tube.

5. A dilator according to claim 1, wherein a screw cap with a closure plate and a central bore is adapted to be fixed to the proximal end of an endoscope shaft, said closure plate having an opening to pass said rod.

6. A dilator according to claim 5, wherein said cap is provided with a conical surface bounding part of said opening to guide said rod.

7. A method of forming and enlarging a path through the human body for subsequent introduction of an endoscopy shaft, said dilator having a distal end to enter the body, and a proximal end, comprising:
    pressing a probe comprising a thin stem with a ball on its distal end into the body; and
    sequentially pressing, one after another, a sequence of concentric tubes, each having a sequentially larger inner and outer diameter, along said stem and over the next smaller tube, the smallest tube first, whereby to enlarge the path, without withdrawal of any tube prior to introduction of the next tube, said rod being within and extending beyond said tubes.

8. A method according to claim 7 in which an endoscope shaft is passed over said telescoped tubes, and the probe and tubes are thereafter withdrawn through said shaft, leaving the shaft in place in the enlarged path.

* * * * *